United States Patent
Narasimha-Iyer et al.

(10) Patent No.: US 10,092,178 B2
(45) Date of Patent: Oct. 9, 2018

(54) SYSTEMS AND METHODS FOR EFFICIENTLY OBTAINING MEASUREMENTS OF THE HUMAN EYE USING TRACKING

(71) Applicant: Carl Zeiss Meditec, Inc., Dublin, CA (US)

(72) Inventors: Harihar Narasimha-Iyer, Livermore, CA (US); Matthew J. Everett, Livermore, CA (US)

(73) Assignee: CARL ZEISS MEDITEC, INC., Dublin, CA (US)

( * ) Notice: Subject to any disclaimer, the term of this patent is extended or adjusted under 35 U.S.C. 154(b) by 74 days.

(21) Appl. No.: 14/688,743

(22) Filed: Apr. 16, 2015

(65) Prior Publication Data
US 2015/0327761 A1 Nov. 19, 2015

Related U.S. Application Data

(63) Continuation of application No. 13/433,127, filed on Mar. 28, 2012, now Pat. No. 9,033,510.
(Continued)

(51) Int. Cl.
*A61B 3/14* (2006.01)
*A61B 3/10* (2006.01)
(Continued)

(52) U.S. Cl.
CPC ............ *A61B 3/102* (2013.01); *A61B 3/0025* (2013.01); *A61B 3/0033* (2013.01); *A61B 3/113* (2013.01);
(Continued)

(58) Field of Classification Search
CPC ......... A61B 3/102; A61B 3/1005; A61B 3/12; A61B 3/1225; A61B 3/1233; A61B 3/0025
(Continued)

(56) References Cited

U.S. PATENT DOCUMENTS

| 4,135,791 A | 1/1979 | Govignon |
| 4,213,678 A | 7/1980 | Pomerantzeff et al. |

(Continued)

FOREIGN PATENT DOCUMENTS

| EP | 0697611 A2 | 2/1996 |
| EP | 2147634 A1 | 1/2010 |

(Continued)

OTHER PUBLICATIONS

Office Action received for Japanese Patent Application No. 2014501631, dated Mar. 1, 2016, 10 pages (5 pages of English Translation and 5 pages of Official Copy).
(Continued)

*Primary Examiner* — Robert E Tallman
(74) *Attorney, Agent, or Firm* — Morrison & Foerster LLP

(57) ABSTRACT

Systems and methods for efficiently obtaining optical coherence tomography (OCT) measurement data with reduced effects of motion are presented. One embodiment involves determining the amount of motion present during the collection of an OCT data set based on images of the eye collected at the same time as the OCT data, and recollecting select portions of the OCT data set when the amount of eye motion is determined to exceed a predetermined threshold. Another embodiment includes enabling or disabling a tracking feature based on the quality of the images available for tracking. Another embodiment includes reducing the effect of motion in the axial direction based on a comparison to a model of the eye constructed from OCT data. The method can also be used to reduce the presence of mirror image artifacts in an OCT image.

27 Claims, 8 Drawing Sheets

Related U.S. Application Data

(60) Provisional application No. 61/516,209, filed on Mar. 30, 2011.

(51) Int. Cl.
*A61B 3/12* (2006.01)
*A61B 3/113* (2006.01)
*A61B 3/00* (2006.01)
*A61B 5/00* (2006.01)
*G06T 7/246* (2017.01)

(52) U.S. Cl.
CPC ............... *A61B 3/12* (2013.01); *A61B 3/145* (2013.01); *A61B 5/0066* (2013.01); *G06T 7/246* (2017.01); *G06T 2207/10101* (2013.01); *G06T 2207/20081* (2013.01); *G06T 2207/30041* (2013.01); *G06T 2210/41* (2013.01)

(58) Field of Classification Search
USPC ........ 351/200, 205, 206, 208, 209, 210, 221
See application file for complete search history.

(56) References Cited

U.S. PATENT DOCUMENTS

| | | | |
|---|---|---|---|
| 4,732,466 A | 3/1988 | Humphrey | |
| 4,768,873 A | 9/1988 | Webb | |
| 4,768,874 A | 9/1988 | Webb et al. | |
| 4,856,891 A | 8/1989 | Pflibsen et al. | |
| 4,937,526 A | 6/1990 | Ehman et al. | |
| 5,321,501 A | 6/1994 | Swanson et al. | |
| 5,471,303 A | 11/1995 | Ai et al. | |
| 5,575,286 A | 11/1996 | Weng et al. | |
| 5,644,642 A | 7/1997 | Kirschbaum | |
| 5,729,008 A | 3/1998 | Blalock et al. | |
| 5,767,941 A | 6/1998 | Ferguson | |
| 5,920,373 A | 7/1999 | Bille | |
| 5,943,115 A | 8/1999 | Ferguson | |
| 5,975,697 A | 11/1999 | Podoleanu et al. | |
| 6,283,954 B1 | 9/2001 | Yee | |
| 6,295,374 B1 | 9/2001 | Robinson et al. | |
| 6,325,512 B1 | 12/2001 | Wei | |
| 6,501,551 B1 | 12/2002 | Tearney et al. | |
| 6,549,801 B1 | 4/2003 | Chen et al. | |
| 6,552,796 B2 | 4/2003 | Magnin et al. | |
| 6,556,853 B1 | 4/2003 | Cabib et al. | |
| 6,655,805 B2 | 12/2003 | Fujieda | |
| 6,726,325 B2 | 4/2004 | Xie et al. | |
| 6,736,508 B2 | 5/2004 | Xie et al. | |
| 6,758,564 B2 | 7/2004 | Ferguson | |
| 6,769,769 B2 | 8/2004 | Podoleanu et al. | |
| 6,788,421 B2 | 9/2004 | Fercher et al. | |
| 6,927,860 B2 | 8/2005 | Podoleanu et al. | |
| 7,072,047 B2 | 7/2006 | Westphal et al. | |
| 7,113,818 B2 | 9/2006 | Podoleanu et al. | |
| 7,118,216 B2 | 10/2006 | Roorda | |
| 7,133,137 B2 | 11/2006 | Shimmick | |
| 7,145,661 B2 | 12/2006 | Hitzenberger | |
| 7,301,644 B2 | 11/2007 | Knighton et al. | |
| 7,330,270 B2 | 2/2008 | O'Hara et al. | |
| 7,365,856 B2 | 4/2008 | Everett et al. | |
| 7,404,640 B2 | 7/2008 | Ferguson et al. | |
| 7,458,684 B2 | 12/2008 | Fukama et al. | |
| 7,480,396 B2 | 1/2009 | Teiwes et al. | |
| 7,512,436 B2 | 3/2009 | Petty et al. | |
| 7,527,378 B2 | 5/2009 | Fukuma et al. | |
| 7,643,154 B2 | 1/2010 | Kikawa et al. | |
| 7,699,468 B2 | 4/2010 | Gaida | |
| 7,755,769 B2 | 7/2010 | Everett et al. | |
| 7,756,311 B2 | 7/2010 | Yasuno et al. | |
| 7,777,893 B2 | 8/2010 | Kikawa et al. | |
| 7,789,511 B2 | 9/2010 | Aoki et al. | |
| 7,805,009 B2 | 9/2010 | Everett et al. | |
| 8,018,598 B2 | 9/2011 | Cense et al. | |
| 8,050,504 B2 | 11/2011 | Everett et al. | |
| 8,079,711 B2 | 12/2011 | Stetson et al. | |
| 8,115,935 B2 | 2/2012 | Everett et al. | |
| 8,306,314 B2 | 11/2012 | Tuzel et al. | |
| 8,363,958 B2 | 1/2013 | Everett et al. | |
| 8,573,776 B2 | 11/2013 | Koizumi et al. | |
| 8,593,514 B2 | 11/2013 | Satake | |
| 8,649,611 B2 | 2/2014 | Everett et al. | |
| 8,857,988 B2 | 10/2014 | Everett et al. | |
| 8,960,903 B2 | 2/2015 | Wirth et al. | |
| 9,033,504 B2 | 5/2015 | Everett et al. | |
| 9,033,510 B2 | 5/2015 | Narasimha-Iyer et al. | |
| 9,101,294 B2 | 8/2015 | Bagherinia et al. | |
| 9,167,964 B2 | 10/2015 | Everett et al. | |
| 2002/0085208 A1 | 7/2002 | Hauger et al. | |
| 2003/0103212 A1 | 6/2003 | Westphal et al. | |
| 2003/0199769 A1 | 10/2003 | Podoleanu et al. | |
| 2003/0227631 A1 | 12/2003 | Rollins et al. | |
| 2005/0024586 A1 | 2/2005 | Teiwes et al. | |
| 2005/0140984 A1 | 6/2005 | Hitzenberger et al. | |
| 2005/0171438 A1 | 8/2005 | Chen et al. | |
| 2005/0219544 A1 | 10/2005 | Chan et al. | |
| 2005/0254008 A1 | 11/2005 | Ferguson et al. | |
| 2005/0270486 A1* | 12/2005 | Teiwes ................... A61B 3/113 351/209 |
| 2006/0119858 A1* | 6/2006 | Knighton ............... A61B 3/102 356/479 |
| 2006/0171503 A1 | 8/2006 | O'Hara et al. | |
| 2006/0187462 A1 | 8/2006 | Srinivasan et al. | |
| 2006/0228011 A1 | 10/2006 | Everett et al. | |
| 2007/0291277 A1 | 12/2007 | Everett et al. | |
| 2008/0025570 A1 | 1/2008 | Fingler et al. | |
| 2008/0100612 A1* | 5/2008 | Dastmalchi ............ A61B 3/102 345/418 |
| 2009/0141240 A1 | 6/2009 | Weitz et al. | |
| 2009/0168017 A1 | 7/2009 | O'Hara et al. | |
| 2010/0027857 A1 | 2/2010 | Wang | |
| 2010/0053553 A1* | 3/2010 | Zinser .................... A61B 3/102 351/206 |
| 2010/0118132 A1 | 5/2010 | Yumikake et al. | |
| 2011/0267580 A1* | 11/2011 | Nakajima .......... G06K 9/00597 351/206 |
| 2011/0267581 A1 | 11/2011 | Nakajima et al. | |
| 2011/0299034 A1 | 12/2011 | Walsh et al. | |
| 2012/0033181 A1 | 2/2012 | Koizumi et al. | |
| 2012/0120408 A1 | 5/2012 | Yasuno et al. | |
| 2012/0140175 A1 | 6/2012 | Everett et al. | |
| 2012/0249956 A1 | 10/2012 | Narasimha-Iyer et al. | |
| 2012/0274783 A1 | 11/2012 | Ko et al. | |
| 2012/0274897 A1 | 11/2012 | Narasimha-Iyer et al. | |
| 2012/0274900 A1 | 11/2012 | Horn et al. | |
| 2012/0277579 A1 | 11/2012 | Sharma et al. | |
| 2012/0307014 A1 | 12/2012 | Wang | |
| 2013/0176532 A1 | 7/2013 | Sharma et al. | |
| 2013/0188140 A1 | 7/2013 | Bagherinia et al. | |
| 2013/0301008 A1 | 11/2013 | Srivastava et al. | |
| 2014/0226130 A1 | 8/2014 | Everett et al. | |
| 2014/0240670 A1 | 8/2014 | Everett et al. | |
| 2015/0062532 A1 | 3/2015 | Sharma et al. | |

FOREIGN PATENT DOCUMENTS

| | | |
|---|---|---|
| EP | 2184006 B1 | 10/2014 |
| JP | 2008509403 A | 3/2008 |
| JP | 2010110392 A | 5/2010 |
| JP | 2010110393 A | 5/2010 |
| JP | 2010249740 A | 11/2010 |
| WO | 2003/082162 A2 | 10/2003 |
| WO | 2003/105678 A2 | 12/2003 |
| WO | 2004/055473 A1 | 7/2004 |
| WO | 2006017837 A2 | 2/2006 |
| WO | 2007/143111 A2 | 12/2007 |
| WO | 2008/002839 A2 | 1/2008 |

(56) References Cited

FOREIGN PATENT DOCUMENTS

| WO | 2010119632 A1 | 10/2010 |
|---|---|---|
| WO | 2012/130976 A1 | 10/2012 |

OTHER PUBLICATIONS

Debuc, Delia Cabrera., "A Review of Algorithms for Segmentation of Retinal Image Data Using Optical Coherence Tomography", Image Segmentation InTech, Chapter 2, 2011, pp. 15-54.
Enfield et al., "In Vivo Imaging of the Microcirculation of the Volar Forearm using Correlation Mapping Optical Coherence Tomography (cmOCT)", Biomedical Optics Express, vol. 2, 2011, pp. 1184-1193.
Jia et al., "Split-Spectrum Amplitude-Decorrelation Angiography with Optical Coherence Tomography", Optics Express, vol. 20, No. 4, Feb. 13, 2012, pp. 4710-4725.
Lujan et al., "Revealing Henle's Fiber Layer Using Spectral Domain Optical Coherence Tomography", Investigative Ophthalmology & Visual Science, vol. 52, No. 3, Mar. 2011, pp. 1486-1492.
Mariampillai et al., "Speckle Variance Detection of Microvasculature using Swept-Source Optical Coherence Tomography", Optics Letters, vol. 33, No. 13, Jul. 1, 2008, pp. 1530-1532.
Nam, et al., "Complex Differential Variance Algorithm for Optical Coherence Tomography Angiography", Biomedical Optics Express, vol. 5, 2014, pp. 3822-3832.
Zhang et al., "Minimizing Projection Artifacts for Accurate Presentation of Choroidal Neovascularization in OCT Micro-Angiography", Biomedical Optics Express, vol. 6, No. 10, 2015, pp. 4130-4143.
Office Action received for European Patent Application No. 06723850. 1, dated Dec. 23, 2009, 3 pages.
Non Final Office Action received for U.S. Appl. No. 11/389,351, dated Dec. 10, 2009, 12 pages.
Notice of Allowance received for U.S. Appl. No. 11/389,351, dated Jun. 7, 2010, 5 pages.
Notice of Allowance received for U.S. Appl. No. 12/075,477, dated Mar. 8, 2010, 7 pages.
Non Final Office Action received for U.S. Appl. No. 12/794,926, dated Apr. 4, 2011, 12 pages.
Notice of Allowance received for U.S. Appl. No. 12/794,926, dated Oct. 11, 2011, 11 pages.
Non-Final Office Action received for U.S. Appl. No. 12/861,672, dated Feb. 23, 2011, 11 pages.
Notice of Allowance received for U.S. Appl. No. 12/861,672, dated Jul. 13, 2011, 5 pages.
Notice of Allowance received for U.S. Appl. No. 13/276,203, dated Sep. 26, 2012, 8 pages.
Non-Final Office Action received for U.S. Appl. No. 13/357,097, dated Sep. 12, 2013, 9 pages.
Notice of Allowance received for U.S. Appl. No. 13/357,097, dated Dec. 17, 2013, 10 pages.
Final Office Action received for U.S. Appl. No. 13/433,127, dated Oct. 7, 2014, 21 pages.
Non Final Office Action received for U.S. Appl. No. 13/433,127, dated Apr. 10, 2014, 17 pages.
Notice of Allowance received for U.S. Appl. No. 13/433,127, dated Jan. 22, 2015, 10 pages.
Final Office Action received for U.S. Appl. No. 13/542,588, dated Apr. 3, 2014, 10 pages.
Non-Final Office Action received for U.S. Appl. No. 13/542,588, dated Sep. 13, 2013, 10 pages.
Notice of Allowance received for U.S. Appl. No. 13/542,588, dated Jun. 12, 2014, 8 pages.
Non-Final Office Action received for U.S. Appl. No. 13/739,193, dated Jun. 13, 2013, 6 pages.
Notice of Allowance received for U.S. Appl. No. 13/739,193, dated Oct. 1, 2013, 7 pages.
Office Action received for Canadian Patent Application No. 2,599,844, dated May 15, 2013, 3 pages.
Podoleanu et al., "Combined Optical Coherence Tomograph and Scanning Laser Ophthalmoscope", Electronic Letters, vol. 34, No. 11, May 28, 1998, 2 pages.
De Boer et al., "Improved Signal-to-Noise Ratio in Spectral-Domain compared with time-domain Optical Coherence Tomography", Optics Express, vol. 28, No. 21, pp. 2067-2069.
Choma et al., "Sensitivity Advantage of Swept Source and Fourier Domain Optical Coherence Tomography", Optics Express, vol. 11, No. 18, Sep. 8, 2003, pp. 2183-2189.
Ehman et al., "Adaptive Technique for high-Definition MR Imaging of Moving Structures", Radiology, vol. 173, No. 1, 1989, pp. 255-263.
Hammer et al., "Advanced Scanning Methods with Tracking Optical Coherence Tomography", Optics Express, vol. 13, No. 20, Oct. 3, 2005, pp. 7937-7947.
Hammer et al., "Image Stabilization for Scanning Laser Ophthalmoscopy", Optics Express, vol. 10, No. 26, Dec. 30, 2002, 8 pages.
Hitzenberger et al., "Three-Dimensional Imaging of the Human Retina by High-Speed Optical Coherence Tomography", Optics Express, vol. 11, No. 21, Oct. 20, 2003, pp. 2753-2761.
Huang et al., "Optical Coherence Tomography", Science, vol. 254, No. 5035, Nov. 22, 1991, pp. 1178-1181.
Ip et al., "Fundus Based Eye Tracker for Optical Coherence Tomography", Proceedings of the 26th Annual International Conference of the IEEE EMBS, Sep. 1-5, 2004, pp. 1505-1508.
Joergensen et al., "Reducing speckle noise on retinal OCT images by aligning multiple B-scan", Coherence Domain Optical Methods and Optical Coherence Tomography in Biomedicine VIII (Bellingham, WA), Proceedings of SPIE, vol. 5316, 2004, pp. 205-213.
McNabb et al., "Quantitative Corneal Refractive Power Measurements Utilizing Distributed Scanning SDOCT", SPIE Photonics West, 8209-13, 2012, p. 82.
Leitgeb et al., "Performance of Fourier Domain vs. Time Domain Optical Coherence Tomography", Optics Express vol. 11, No. 8, Apr. 21, 2003, pp. 889-894.
Leitgeb et al., "Ultrahigh Resolution Fourier Domain Optical Coherence Tomography", Optics Express, vol. 12, No. 10, May 17, 2004, pp. 2156-2165.
Li et al., "Automatic Montage of SD-OCT Data Sets", Optics Express, vol. 19, No. 27, Dec. 19, 2011, pp. 26239-26248.
Mulligan, Jeffrey B., "Recovery of Motion Parameters from Distortions in Scanned Images, Proceedings of the NASA Image Registration Workshop (IRW97)", Goddard Space Flight Center, Maryland, 1997, 15 pages.
Naess et al., "Computer-Assisted Laser Photocoagulation of the Retina-a Hybrid Tracking Approach", Journal of Biomedical Optics, vol. 7, No. 2, Apr. 2002, pp. 179-189.
Nassif, N. A. et al., "In Vivo High-Resolution Video-Rate Spectral-Domain Optical Coherence Tomography of the Human Retina and Optic Nerve", Optics Express vol. 12, No. 3, Feb. 9, 2004, pp. 367-376.
International Search Report and Written Opinion received for PCT Patent Application No. PCT/EP2006/002883, dated Nov. 28, 2006, 12 pages.
International Preliminary Report on Patentability received for PCT Patent Application No. PCT/EP2012/055684, dated Oct. 10, 2013, 10 pages.
International Search Report and Written Opinion received for PCT Patent Application No. PCT/EP2012/055684, dated Jul. 5, 2012, 13 pages.
International Preliminary Report on Patentability received for PCT Patent Application No. PCT/EP2012/063191, dated Jan. 16, 2014, 8 pages.
International Search Report and written opinion received for PCT Patent Application No. PCT/EP2012/063191, dated Dec. 4, 2012, 8 pages.
Rogers et al., "Topography and Volume Measurements of the Optic Nerve using En-Face Optical Coherence Tomography", Optics Express, vol. 9, No. 10, Nov. 5, 2001, pp. 533-545.
Stevenson et al., "Correcting for Miniature Eye movements in high resolution Scanning Laser Ophthalmoscopy", Proceedings of the SPIE, vol. 5688, 2005, pp. 145-151.

(56) References Cited

OTHER PUBLICATIONS

Zawadzki et al., "Cellular Resolution Volumetric in Vivo Retinal Imaging with Adaptive Optics—Optical Coherence Tomography", Optics Express, vol. 17, No. 5, Mar. 2, 2009, pp. 4084-4094.
Notice of Allowance received for U.S. Appl. No. 11/331,567, dated Dec. 13, 2007, 8 pages.
Non-Final Office Action received for U.S. Appl. No. 12/075,477, dated Oct. 19, 2009, 8 pages.
Notice of Allowance received for U.S. Appl. No. 14/153,993, dated Jan. 23, 2015, 8 pages.
Non-Final Office Action received for U.S. Appl. No. 14/484,038, dated Dec. 14, 2015, 14 pages.
Hammer et al., "Active Retinal Tracker for Clinical Optical Coherence Tomography Systems", Journal of Biomedical Optics, vol. 10, No. 2, Mar./Apr. 2005, pp. 024038-1-024038-11.
International Preliminary Report on Patentability received for PCT Patent Application No. PCT/EP2006/002883, dated Oct. 9, 2007, 9 pages.
International Search Report and Written Opinion received for PCT Patent Application No. PCT/EP2013/000152, dated Jun. 27, 2013, 16 pages.
Invitation to Pay Additional fees received for PCT Patent Application No. PCT/EP2013/000152, dated May 3, 2013, 5 pages.
Podoleanu et al., "Combined Multiplanar Optical Coherence Tomography and Confocal Scanning Ophthalmoscopy", Journal of Biomedical Optics, vol. 9, No. 1, Jan./Feb. 2004, pp. 86-93.

\* cited by examiner

SYSTEMS AND METHODS FOR EFFICIENTLY OBTAINING MEASUREMENTS OF THE HUMAN EYE USING TRACKING

PRIORITY

This application is a continuation of U.S. patent application Ser. No. 13/433,127, filed Mar. 28, 2012, which claims priority to U.S. Provisional Application Ser. No. 61/516,209, filed Mar. 30, 2011, each of which is hereby incorporated by reference in its entirety.

TECHNICAL FIELD

One or more embodiments of the present invention relates generally to improvements in data acquisition in ophthalmic diagnostic systems. In particular, it is an object of the present invention to reduce the effects of eye motion in the collected data and to do so in an efficient fashion.

BACKGROUND

There are useful scanning ophthalmic diagnostic devices that build up a map of measurements of the retina of a patient. This can be accomplished using different imaging modalities such as optical coherence tomography (OCT) and scanning laser polarimetry (SLP). Examples of two such commercial devices are Stratus OCT and GDx, both manufactured and sold by Carl Zeiss Meditec, Inc. (Dublin, Calif.). In the time (usually a few seconds) required to build a useful map, the patient's gaze can shift, causing the retinal image to move from the point of view of the ophthalmic device. Retinal tracking has been used to follow and correct for eye motion. In this case, the scanning beam is adjusted to compensate for movements and collect data from the optimal location. For example, systems have been described that detect apparent motion of the retina using a tracking beam and move mirrors in the imaging path to provide a stabilized OCT image (see for example U.S. Pat. Nos. 6,736,508, 6,726,325 and 6,325,512). Additionally U.S. Pat. No. 7,805,009 describes the use of a line scan ophthalmoscope to monitor the position of the eye and apply a correction to the OCT scanner. The GDx instrument takes a different approach; instead of stabilizing the retinal image, GDx registers the 32 successive retinal images, each imaged using a different illumination polarization, to make the polarimetry map. Even with tracking or registration, there are however, situations that cause some of the measurement data to be unusable. If there is motion or a blink that occurs before the tracker has determined that there was motion, data collected up to that point would likely contain motion artifacts and would likely be unusable for measurement and diagnostic purposes. If the patient rapidly shifts their gaze in a saccadic motion, the data taken before the tracker had a chance to compensate would be measured at the wrong location on the retina. The methods described above do not address this missing data problem. For example, the method described in U.S. Pat. No. 7,805,009 uses a line-scan imager to monitor the retina for motion. Each line of image data from the line scan imager is compared with a reference image to find the displacement of the subject that can be used to correct the OCT image data. This has the limitation that it cannot handle large and sudden movements such as saccades. Also none of the methods described above account for motion of the subject along the axial direction.

Prior art tracking systems, repeat one line of the OCT measurement sequence until sufficient data is collected while the retinal image is reasonably stable, but they do not continue scanning, determine that there was motion and then go back to retake data missed due to eye motion. Also prior art instruments do not provide the user a way to control the tracking and to obtain the data in an efficient way in the shortest possible time. Another concern with the current tracking devices is that the time for an acquisition is considerably longer than without tracking because the tracker keeps retrying to acquire the data if the eye is not stable.

It is therefore an object of the present invention to provide systems and methods for retinal tracking that overcome the above identified limitations.

SUMMARY

One or more embodiments of the present invention satisfy one or more of the above-identified needs in the prior art. In particular one embodiment of the present invention provides a system and method to efficiently acquire data in the presence of motion using the following elements:
1) A measurement system for acquiring ophthalmic measurements.
2) An imaging system that produces images of the eye to be used by the tracking system to analyze motion.
3) A synchronization mechanism between (1) and (2).
4) A quality monitoring system that analyzes the images of the eye to decide if they are of sufficient quality for tracking purposes, additionally this system helps to select the best image to be used as a reference image for the tracking system described next.
5) A tracking system capable of determining if the eye has moved based on a comparison to a reference image or frame. The tracking system can detect motion in any or all of the x, y, and z dimensions.
6) A decision system that decides based on the input from the tracking system, the measurement system, and some other pre-defined criteria whether the acquired data is acceptable. If it is acceptable, the measurement data is kept. If it is not, it instructs the measurement system to go back and rescan the data optionally with computed offsets to compensate for motion.
7) A user interface system that displays relevant information to the user and gets inputs from the user for the different systems as needed.

Key aspects of the invention include a method to determine the quality of the images of the eye for tracking purposes. The quality determination can be used to turn tracking on and off and can be continuously monitored to identify when a superior reference frame becomes available. This ensures that the best reference frame is selected for tracking purposes. The reference frame can be from the current examination or a previous examination, allowing for the possibility of repeat scanning at the same location as a previous measurement. Another key aspect of the invention is the decision system. It provides the ability to determine when to go back and re-scan the measurement data based on different inputs to the system or when to continue on with data collection if the scan has exceeded a predetermined amount of time. Furthermore the invention provides a method to track motion in the axial direction.

Different embodiments of the invention can be imagined by one skilled in the art and various embodiments may not require all of the above described elements to fall within the scope of the invention. While the detailed description focuses on the retina in the posterior section of the eye, aspects of the invention could also be applied to other regions of the eye including the anterior region. It is to be understood that both the foregoing general description and the following detailed description are exemplary and explanatory only and are not restrictive of the invention, as claimed.

DETAILED DESCRIPTION

Figure 1:
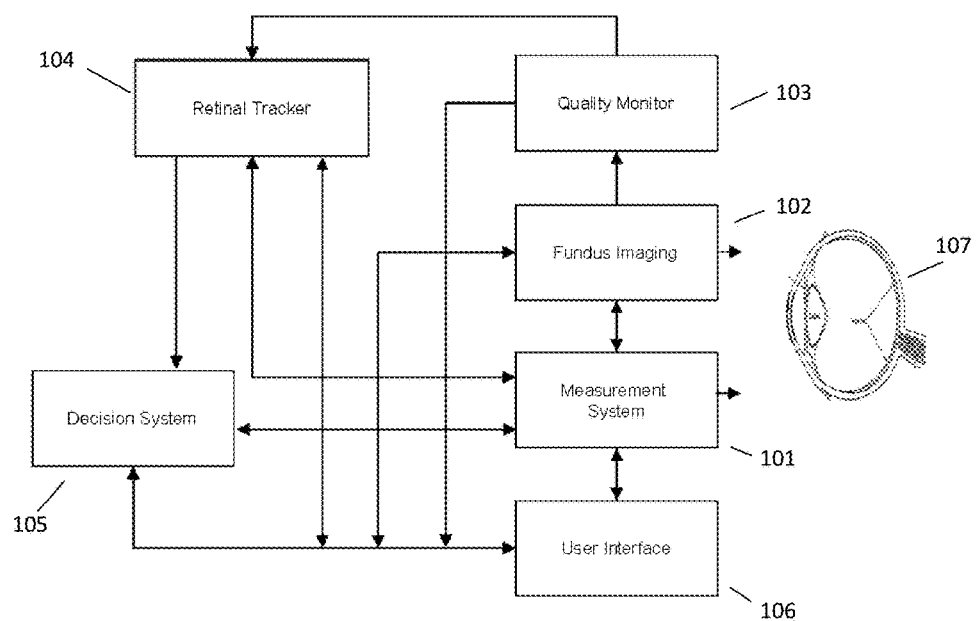
FIG. 1 is a block diagram of the key components of one embodiment of the present invention.

FIG. 1 shows a block diagram of the key components for one possible implementation of the current invention. Each of the components in the figure will be described in detail below.

Measurement System

The measurement system 101 can be any system that measures some structural or functional property of the eye 107 including but not limited to Optical Coherence Tomography (OCT), Polarimetry, or Microperimetry.

Fundus Imaging System

The fundus imaging system 102 can be any system that produces an image of the eye 107 that can be used to detect motion by the tracking system. For example, fundus images can be produced by reflectance imaging or angiography, acquiring single or multiple points at a time. Ideally fundus images would be collected in rapid succession, providing a stream of images for use in tracking. Methods for deciding on whether or not a particular fundus image will be suitable for tracking purposes will be described in detail below. The methods described herein can apply to both partial and full images generated by the fundus imaging system as would be possible in the case of line or spot scanning ophthalmoscopes.

The fundus imaging system and the measurement system are synchronized such that with any measurement data, a corresponding fundus image can be identified. The measurement data is not constrained to one per fundus image and in fact it can be multiple measurements (For example, multiple OCT B-scans) corresponding to one fundus image.

Figure 2:
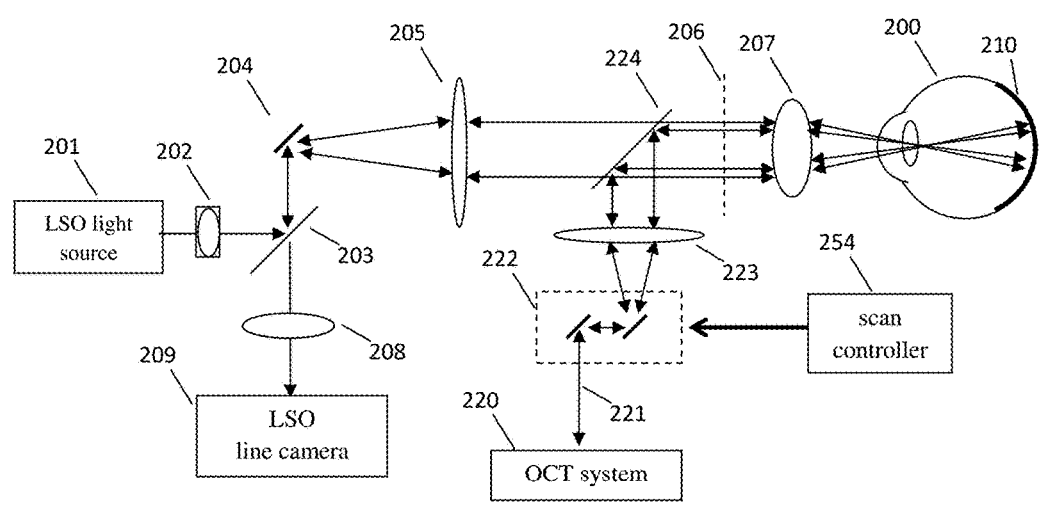
FIG. 2 illustrates a specific measurement and imaging system combination that could be used in an embodiment of the present invention.

A specific measurement and fundus imaging system combination using the invented methods described herein combines an OCT scanner and a line-scan ophthalmoscope (LSO) as described in U.S. Pat. No. 7,805,009 hereby incorporated by reference and illustrated in FIG. 2. As mentioned above, the imaging device can be any imaging system capable of capturing an image of the eye including but not limited to, a confocal scanning laser ophthalmoscope (cSLO), a fundus camera, a LSO, or an OCT system.

Light from the LSO light source 201 is routed by cylindrical lens 202 and beamsplitter 203 to scanning mirror 204. The cylindrical lens 202 and the scan lens 205 produce a line of illumination at the retinal image plane 206, and the ocular lens 207 and optics of the human eye 200 re-image this line of illumination onto the retina 210. The line of illumination is swept across the retina as the scanning mirror 204 rotates. Reflected light from the retina approximately reverses the path of the LSO illumination light; the reflected light is scanned by the LSO scan mirror 204 so that the illuminated portion of the retina is continuously imaged by imaging lens 208 onto the LSO line camera 209. The LSO line camera converts the reflected LSO light into a data stream representing single-line partial images, which are processed to form both eye tracking information and a real-time display of the retina.

The OCT system 220 incorporates the light source, light detector or detectors, and processor required to determine the depth profile of backscattered light from the OCT beam 221. The OCT system can use time or frequency domain methods (spectral domain, swept-source, etc. see for example U.S. Pat. No. 5,321,501 and US Publication No. 2007/0291277 hereby incorporated by reference). OCT scanner 222 sweeps the angle of the OCT beam laterally across the surface in two dimensions (x and y), under the control of scan controller 254. Scan lens 223 brings the OCT beam into focus on the retinal image plane 206. Beamsplitter 224 combines the OCT and LSO beam paths so that both paths can more easily be directed through the pupil of the human eye 200. (Combining the beam paths is not required in direct imaging applications, where the object itself lies in the location of the retinal image plane 206.) If the OCT and LSO use different wavelengths of light, beamsplitter 224 can be implemented as a dichroic mirror. The OCT beam is re-focused onto the retina through ocular lens 207 and the optics of the human eye 200. Some light scattered from the retina follows the reverse path of the OCT beam and returns to the OCT system 220, which determines the amount of scattered light as a function of depth along the OCT beam. Each line of data in the axial or depth direction (z-direction) is called an A-scan. A cross-sectional tomograph, or B-scan, can be obtained by laterally combining a series of A-scans. A variety of ways to create B-scans are known to those skilled in the art including but not limited to along the horizontal or x-direction, along the vertical or y-direction, along the diagonal of x and y, or in a circular or spiral pattern. The majority of the examples discussed herein refer to B-scans in the x-z dimensions but the invention would apply equally to any cross sectional image.

It will be evident to those skilled in the art that this invention can be applied to other measurement and imaging systems to provide measurement data with reduced effects from motion. In addition the methods could be applied to other types of data suitable for tracking purposes, not just two-dimensional fundus image data described in detail here. For example, the information might be 1D signals along the z-dimension to track the axial motion or even 3D range data that could be used to track the eye in all 3-dimensions.

Fundus Quality Monitoring System

The retinal tracking system 104 uses the images from the fundus imaging system 102 for determining the motion of the retina of the eye of the patient 107. In order to do this, the retinal tracker needs a reference image or frame. Subsequent "live" images from the fundus imaging system are compared against the reference image for deciding if there was motion. Hence the ability of the tracker to function properly depends on the quality of the fundus images. The monitoring system described herein uses a processor to automatically determine the quality of the fundus images 103. A determination of the quality of the images ensures optimal performance of the tracker in determining motion and provides an option to turn tracking on or off either based on user input or automatically without any user intervention. This ability is important for the following reasons:

1) The ability to automatically turn on tracking with no manual step simplifies the workflow and will give an advantage over systems that have tracking that needs to be manually activated.
2) The ability of the tracking algorithm to lock on to subsequent frames depends to a large extent on the features that can be extracted from the reference frame. Hence it is desirable to ensure that the reference frame is of sufficient quality for tracking to streamline the workflow.
3) Processor resources are needed to initialize and track. Hence it is desirable not to load the processor with the tracking algorithm until there exists a sufficient quality fundus image stream to track.
4) The algorithm may also be used to check the quality of the incoming frames intermittently once tracking is enabled to monitor if a better fundus image is available for use as the reference frame.

The determination of the fundus image quality can be based on a combination of factors such as the focus of the image, uniformity of illumination, contrast etc. One such implementation might be to combine two different factors as given below:

$$Q = \mu_1 q^{int} + \mu_2 q^{focus},$$

where Q is the overall quality metric, $q^{int}$ is a metric based on the overall brightness or intensities of the pixels in the image, $q^{focus}$ is a metric based on whether the image is in good focus. $\mu_1$ and $\mu_2$ are multiplication factors to weight the individual factors of the quality metric. Non-equal weights are given to the two components to represent their importance to good feature extraction for tracking performance. The final metric is defined on a range of 0 to 10, 0 being the "worst" quality image and 10 being the "best" quality image.

One possible implementation of $q^{int}$ is based on the mean brightness of the current image and the mean brightness of a representative set of images that are known to provide good tracking performance. In this case, $q^{int}$ can be defined as:

$$q^{int} = \frac{I_{mean}}{I_{meanStandard}} * ScalingFactor \quad I_{mean} < I_{meanStandard},$$

$$q^{int} = ScalingFactor \quad I_{mean} \geq I_{meanStandard}.$$

where $I_{mean}$ is the mean brightness of the current image being processed and $I_{meanStandard}$ is the brightness calculated from a representative set. Scaling Factor is a multiplier factor used for scaling. If $I_{mean}$ is greater than $I_{meanStandard}$, then $q^{int}$ is clipped to ScalingFactor. This means that the quality factor is trying to describe a baseline for the overall brightness. If the brightness is above this baseline, it does not affect the score anymore.

One possible implementation of $q^{focus}$ is based on derivatives of the image intensities in the current image and the expected value for the same measure from a representative set of images that are known to provide good tracking performance. In this case, $q^{focus}$ can be defined as:

$$q^{focus} = \frac{dI_{curr}}{dI_{standard}} * ScalingFactor \quad dI_{curr} < dI_{standard},$$

$$q^{focus} = ScalingFactor \quad dI_{curr} \geq dI_{standard}$$

where $dI_{curr}$ is a measure of the high frequency content in the image calculated by summing up the derivatives in x and y directions over the whole image. $dI_{standard}$ is the same measure calculated from a standard set of images. It is possible to vary the weighting given to each component of the image quality using the multiplication factors $\mu_1$ and $\mu_2$ used in the computation of the overall quality metric.

Figure 3:
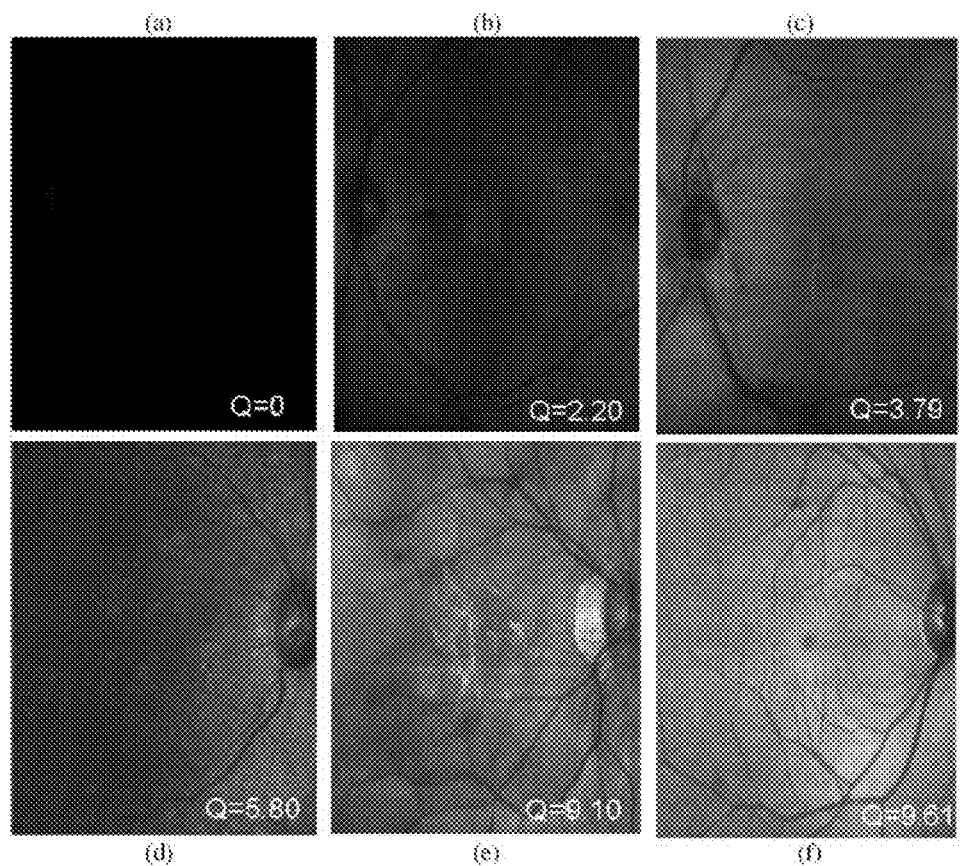
FIG. 3 illustrates a series of fundus images of various qualities and their corresponding quality metric as determined by one aspect of the present invention.

FIG. 3 shows some sample fundus images with increasing quality as determined by the automatic algorithm described above. The numerical value of the quality metric ranges from 0 to 9.61 for images (a)-(f).

The quality metric described above is only one example of a possible implementation and those skilled in the art can implement other versions of the measure. The main idea is to capture the suitability of a fundus image to be used for tracking whether as a reference image or as a "live" image.

The quality metric can be used to evaluate the fundus image stream to determine when to start tracking prior to measurement acquisition. For example, a threshold can be established for the quality metric and tracking can only be initiated when the quality of the incoming images has been above the threshold for a particular amount of time with no significant breaks in between.

Prior to measurement acquisition, the quality metric could be used to constantly monitor the incoming frames from the fundus imaging system to select an image with sufficient quality to be used a reference frame. Subsequent frames could also be monitored to see if a better image becomes available and the reference image could be replaced at this point if needed. If the patient shifts their gaze to a new location and then maintains fixation at that new location, it would be desirable to reset the reference frame to the new location and maintain tracking at this location going forward. This can automatically be done by checking a measure of distance between the current reference frame and the live images (i.e. the shift between landmark locations). If it is found that the "distance" is high and is consistently high then the reference frame could be reset to be an image acquired at the new fixation location. If the patient only temporarily changes their gaze location, the reference frame would be shifted back using the same principle.

The quality metric could also be displayed to the user using a graphical user interface 106 (GUI) and this would provide visual feedback to the user to better align the patient to improve the quality of the fundus image as needed. This could be accomplished in a variety of ways including a numeric display of the actual index, a quality bar, or a simple colored reference indicator that switches between colors depending on the quality of the image frame. In subjects where media opacities or pathologies prevent a good fundus image from being captured, this quality indication mechanism will provide the user with feedback about the unsuitability of the fundus image for tracking so that the operator could switch off tracking if needed to save time and improving workflow.

Retinal Tracker

The retinal tracker 104 carries out a comparison between a reference image and a subsequent image to determine motion. While any image could be used as a reference, the preferred embodiment of the invention takes as input a reference image which is of sufficient quality for tracking as determined by the quality monitoring system 103 described above. As previously mentioned, the images used by the tracker might be from a variety of different modalities such as reflectance imaging or angiography or may be other types of data suitable for use in tracking motion of the retina. As will be discussed below, the reference image can come from data collected on the patient at a previous point in time. While the measurement system is acquiring data, the retinal tracker compares the reference image to "live" images that are obtained concurrently and synchronized with the measurements. Prior to measurement data acquisition (initialization mode), the tracker can compare the reference image to subsequent images from the live stream in an effort to obtain the most accurate reference image for tracking. For example, if it was determined that a subsequent image frame was significantly displaced relative to the reference frame, as would be the case if the patient's fixation changed, the new frame could be selected as the reference frame for subsequent comparisons. This allows the tracking system to operate the most efficiently with minimized processing requirements and with the highest probability for success.

The tracker determines based on the live image and the reference image how much motion there was between the reference frame and the live image. This could be done by using information from the whole image or by using portions of the images. The portions of the images could be selected for example based on distinct features in the image such as blood vessel junctions and bifurcations, optic disc etc. The portions of the image might also be predefined regions in the images. One possible implementation is to detect the blood vessels in the image and find the vessel junctions and bifurcations and use them as stable features for determining the motion between frames.

Figure 4:
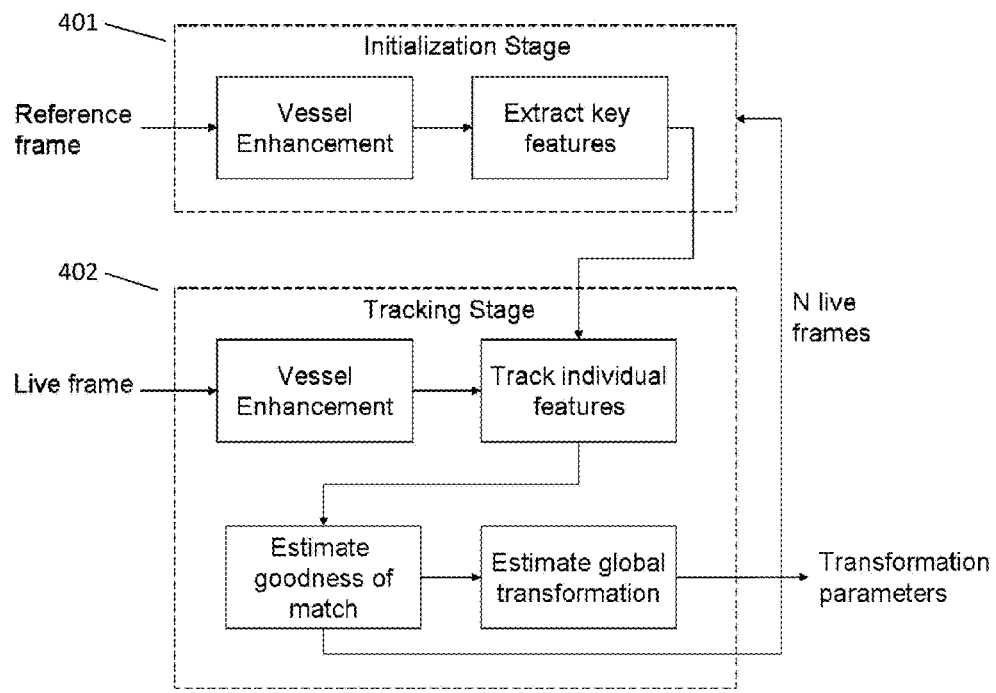
FIG. 4 illustrates the steps in the initialization and tracking stages of the invention.

FIG. 4 shows a block diagram of a retinal tracking system with this implementation. The tracking process is broken into two stages: initialization 401 and tracking 402. In the case of an automatic algorithm, the key step in the initialization stage is to ensure that stable features are selected from the set of possible features in the reference image. An additional optional aspect of the invention is to provide enhancement of the vessels prior to extraction of key features. This could be accomplished in a number of ways including averaging several live frames to create a composite reference frame with better quality (see for example US Publication No. 2005/0270486 hereby incorporated by reference). In the invention described here, the quality of the features is ensured in two ways. First, only images that are of a minimum quality as determined by the quality monitoring system are selected as reference frames. Second, adaptive "learning" is used to determine the best features for tracking based on tracking N frames that are captured after the reference frame. This leaning process will be described after a description of how the motion might be determined between two frames.

Given that a set of features exist in the reference frame, their corresponding location in the live frames can be determined by finding the best match location using a metric such as normalized cross correlation (which is insensitive to intensity variations) or sum squared error. Once all the potential matches are obtained, the matches can be further pruned based on the quality of the match (such as a threshold on the normalized correlation metric). Outliers in the matches can also be found based on robust estimation techniques which are well known in the field. From the "good" matches, a global transformation between the reference frame and the live frame can be determined. This transformation can be as simple as a translation only, translation and rotation, or higher order transformations that account for magnification, projection errors etc. The transformation that is computed here determines the amount of motion between the live frame and the reference frame. Based on the region that is being measured in the fundus image, the maximum error (i.e. distance in microns) can be calculated between where a measurement was supposed to be and where it actually was while the live fundus image was acquired. This error is referred to as "scanning error" in the rest of this document.

The learning process of selecting the best features depends on storing the information for "good" matches for N subsequent frames after the reference frame. Features that are detected as "outliers" in the N frames frequently tend to belong to artifacts in the reference image such as reflections and noise. Hence using the tracking results themselves from a set of subsequent frames, the tracking performance could be improved. One important advantage of pruning the feature set as described above is to decrease the processing time for computing the transformation between the live frame and the reference image. It is desirable that the estimation of the transformation happens as close to real-time as possible although this is not a necessity in the invention described herein.

Once the relative motion between the two images is known and the scanning error is computed, the information is passed on to the decision system 105.

Note that the reference frame may be obtained from a previous examination of the patient. In this way, the measurement can be made from the same location as from the previous examination. Alternatively, it is possible to register an old fundus image to the current reference frame and then use the displacement information between those two frames and the displacement between the reference frame and the live frames to acquire measurements at the same location as the previous scan. In this case the old fundus image could have been taken using the same imaging modality or a different imaging modality as long as the features apparent in the image are able to be correlated to the features in the imaging modality being used for tracking using manual or automated means. The second approach is preferable because it is to be expected that a reference frame from the current session will be easier to track to as compared to a fundus image from a previous session which might be different anatomically due to changes.

Tracking Z-Position

A further aspect of this invention is to monitor the position of the eye in the axial or z-direction to reduce the effects of motion in the depth direction of measurement data. As for the x and y tracking, the invention could apply to both posterior and anterior regions of the eye. The retina is used as an illustrative example. A fundus image is typically a 2D image that does not give depth information or the distance of the subject from the measurement system. However for a measurement system such as an OCT scanner, where the measurements are made along the z-direction (perpendicular to the x-y plane as imaged by the fundus imaging system), the information in the depth direction could also be utilized by the retinal tracker and the decision system either alone or in combination with tracking in the x and y dimensions.

This is especially important since for an OCT system, even if the eye is positioned properly in the x and y or lateral dimensions, the eye may not be positioned properly along the axial or z-direction. To get good data, the depth location within the sample being imaged must be set within the capture range of the OCT system, typically by a translatable mirror in the reference or sample arm. OCT systems have limited depth or axial ranges determined by the sampling interval or resolution of the optical frequencies recorded by the OCT system. If the depth location of the system relative to the sample is not set correctly, or the patient moves, there can be problems where the data is cut-off at the top or bottom or only partial data is available along the z direction even though the scan was acquired at the correct x-y location. Attempts to correct axial motion in post-processing of image data have been made based on performing autocorrelations between A-scans and shifting the data accordingly. There are limits over the range of motion these types of methods can work and it would not be determined until after the data collected that the motion occurred, possibly creating problems in using the data for diagnostic purposes.

Figure 5:
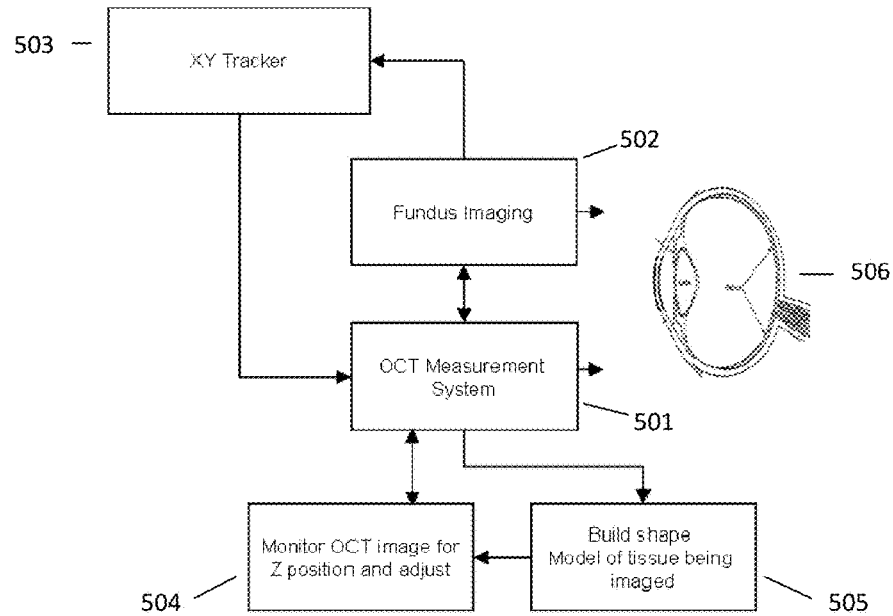
FIG. 5 is a block diagram of the key components of an embodiment of the invention directed towards reducing the effects of motion in the axial or depth direction.
Figure 6:
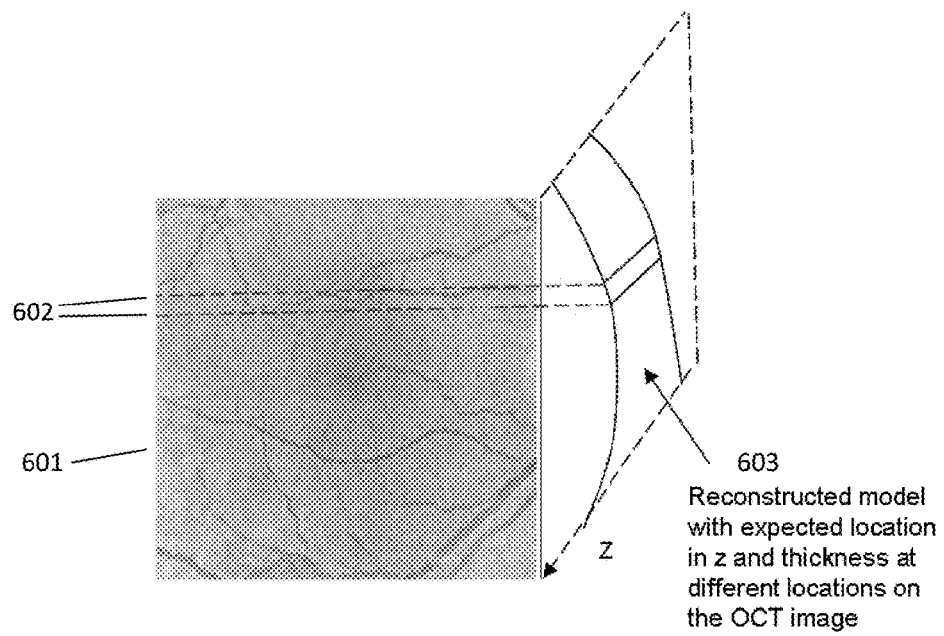
FIG. 6 illustrates a model of the axial structure of the eye and how it can be used to verify positioning of subsequent B-scans.

FIG. 5 shows a possible implementation of z-tracking for an OCT system that could overcome the limitations of the prior art. In this embodiment using an OCT scanner 501, before the start of the actual scan acquisition, an approximate model of the shape of the region being imaged is built using a number of quick OCT B-scans 505. One possible implementation is to acquire three horizontal scans spaced over the region of interest to be scanned. Using the depth information from these three B-Scans, an approximate model for the whole region being imaged can be built. The model provides a range of acceptable z-values for subsequent data. FIG. 6 shows an en face OCT image 601 with a corresponding model along the z-axis 603 reconstructed from a few fast B-scans as described above. This model is used as a reference for the expected z-location and thickness for a particular location on the retina that is being scanned 602. Any number of B-Scans could be acquired and used to build the model as long as they are taken in a time where the eye is relatively stable along the axial dimension. Additionally the model could be built from B-scans acquired in a previous examination of the patient. One example of how a model can be built is as follows:

1) For each B-Scan, find the region of the tissue in the image using a thresholding scheme where the tissue is identified as the regions in the image where the intensity is greater than a particular threshold. The threshold can be adaptive and can be calculated based on the characteristics of the signal and noise in the image itself.

2) Once the tissue region is determined, the absolute top and bottom z-axis values of the tissue for the particular B-Scan can be identified.

3) Using the top and bottom points from the three B-Scans described earlier, a model can be built based on fitting a quadratic polynomial to the set of top and bottom points separately (or other fitting methods such as splines). The approximate z-location of each B-Scan in the dataset can also be determined. This can be the centroid of the model that was fit.

During the scan acquisition, the tracker could find the top, bottom and center of the tissue in the OCT image and the decision system could use the expected z location calculated as a reference using the model to see if the image is appropriately placed along the z-axis. This could include checking the top, bottom and centroid of the OCT image in the current frame with preset limits and deciding if the tissue is properly placed in the image or could be accomplished by matching other landmarks or layers determined in the model to the OCT data being collected. If it determined that the OCT data is not within the acceptable range of values, the data could be retaken or the depth location adjustment (i.e. reference mirror location) could be changed to put the depth location within the acceptable range and ensure the success of post-processing methods.

Another possibility is to pre-program the z-position model into the measurement system so that the measurement system adjusts itself to the varying anatomy automatically. For example, for an OCT scanner, it will be possible to change the reference mirror location to position the image appropriately based on the pre-computed model and use the tracking data to move the reference mirror as necessary throughout data acquisition.

Mirror Artifact Detection

A common issue with OCT images is the "reflection" problem where the mirror image can appear and complicate an OCT image when the tissue is located sub-optimally along the z-dimension. Using the method described earlier for finding the top, bottom and center of the image, the mirror image would also be accepted by the decision system since the mirror image can appear in the same location as the actual image. A method is described here for detecting a reflected signal and informing the decision system of its presence so that the decision system can instruct the measurement system to retake the data as needed. One possible embodiment for doing the reflection detection is as follows.

It is known in the field of OCT that the reflected image can be blurred out compared to the good image based on chromatic dispersion differences in the arms of the interferometer (see for example U.S. Pat. No. 7,330,270 hereby incorporated by reference). This leads to the observation that the gradients, or intensity differences between neighboring pixels, are weaker in the reflected image than in the good image. Calculation of image gradients is well known in image processing. The gradients can be calculated for points along the lateral and axial dimensions independently and can be combined to provide a metric that corresponds to the sharpness of the image. Since the blurring is more along the axial dimension as compared to the lateral dimension, the gradients along the two dimensions could also be weighted differently. The combined measure of the gradients can be normalized with respect to the actual intensities in the image to take into account varying signal properties across images. Once this normalized measure is calculated, it could be compared with a threshold computed from a range of images to make a decision of whether the image under consideration is reflected. It is expected that the normalized measure would be lower for reflected images and higher for normal images since it is measuring the blurriness of the image. OCT images with the measure less than the threshold are considered mirror images and OCT images with the measure greater than the threshold are considered normal images. This information can be given as another input to the decision system and OCT data with reflected image can be rejected and normal images can be accepted.

An alternative method for identifying the reflected image would be to use the curvature of the data as a way to evaluate the data and determine if data should be reacquired and/or if the reference mirror should be adjusted. One example of this would be accepting only the data that appears concave with increasing depth values and rejecting data that appears convex with increasing depth values.

Decision System

The decision system 105 is responsible for deciding whether to accept or reject the measurement data associated with each fundus image. If it is accepted, the measurement data is kept and the measurement system is informed that the data is good. However if the data is not accepted, the decision system informs the measurement system to re-take the data with some particular offset. The decision system could be running on a separate processor or could share resources with the same processing unit that runs one or more of the other systems described above. When the term processor is used in the claims, it is intended to encompass single or multiple processors for carrying out the various steps of the invention.

In order to make a decision about whether to accept or reject the data, the decision system can use a number of inputs. The inputs include but are not limited to:
1) Scanning error for current frame
2) Scanning error for subsequent frame
3) The detected z-position of the measurement data (if applicable)
4) Expected spatial x,y location of the measurement data
5) Expected spatial z location of the measurement data (if applicable)
6) Time elapsed since start of measurement acquisition
7) The time remaining to the end of measurement acquisition
8) The desired "accuracy" of the measurement data In addition to the amount of motion detected from the current live frame, the decision system could also use information from the motion detected in the subsequent live frames. This information could be used to make the decision more robust. There is a finite time window associated with acquisition of a fundus image. Motion occurring towards the end of the time window might be missed by the tracker. However if there was real motion, the motion would be detected from the next frame. Hence having the motion information from multiple frames makes the decision of whether to accept/reject measurement data more robust. Motion information from multiple frames could also be used to predict the future location of the retina. This information can be fed back to the measurement system when it is asked to retake measurements.

The spatial location (x,y) of the measurement data is the relative position of the measurement data with respect to the set of measurements being made in the x-y plane. For example, an OCT cube-scan can consist of a set of B-Scans acquired in a rectangular region of the retina and displaced from each other by a particular offset. Hence each B-Scan has an expected location in the cube and an expected region in the retina that it will image. For an OCT scan, an expected position in z exists based on the model construction as described earlier or based on information from a previous scan that was obtained.

Another important parameter is the total time that is allowed for a particular acquisition of measurement data. The tracking system can also measure the time elapsed since the start of a particular measurement acquisition. From the above two parameters, it is possible to calculate the time remaining to the end of the measurement acquisition. The time allowed for a particular scan could be based on the amount of measurement data that is desired to be collected and on the particular scan type that is being used. It could also be provided by the user as input to the system.

The "accuracy" is defined as the amount of "acceptable motion" or the scanning error that the decision system will tolerate before it decides to go back and rescan data. This can be a constant or a variable value that may be changed during the acquisition. The looser this parameter is the faster the scan will be since it accepts more errors. The decision to choose this parameter might be based on how well the patient can fixate, how much accuracy is needed in the underlying measurement and how much time the user is willing to wait to acquire the data. This single parameter captures the trade-offs between all the above considerations. This concept of configurable "accuracy" is a key aspect of the present invention. It should be noted that separate accuracy parameters could apply to x, y and z dimensions or that a single accuracy parameter could be used to evaluate multiple dimensions together, i.e. x and y. In a preferred embodiment of the invention, one accuracy parameter is used for the z dimension and one parameter is used for the x and y dimensions jointly.

Figure 7:
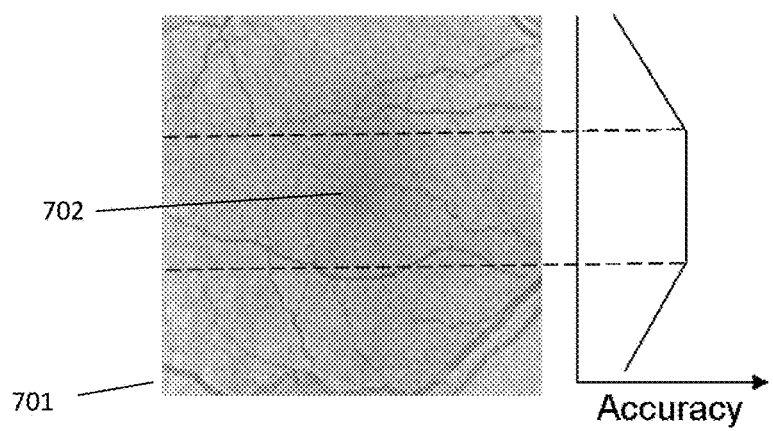
FIG. 7 illustrates the concept of a spatially varying accuracy parameter for use in the present invention.

The user may specify the accuracy parameter(s) at the beginning of the scan. In this case, it will be a constant through out the scan. In another scheme, the user might wish to give more importance to particular locations of the measurement and hence tolerate lesser errors in the measurement location in such regions. For example, FIG. 7 shows a 2D projection 701 of OCT cube-data of the macular region of the eye. It also shows one embodiment of how the accuracy parameter may be varied spatially across the different regions of the image. The fovea 702 in the central portion of the eye is the most important region affecting the vision of the eye. In the illustration here, the central portion in the image contains the fovea and is given the best accuracy. The data towards the periphery is progressively less important and hence the accuracy can also be reduced in these regions resulting in faster acquisition of data over these regions. The accuracy parameter could also be varied depending on the acquisition time, i.e. being high at the beginning of a scan and lower as less time is available to finish the scan. Additional embodiments of varying the accuracy parameter can be imagined by one skilled in the art.

In the case of OCT where the z-dimension is measurable, the accuracy parameter could be made a function of the local thickness of the tissue being imaged. It could also be varied temporally.

The decision system combines the data from all the inputs and decides if a measurement or measurements needs to be re-taken. In one implementation of the present invention, the user sets a constant threshold(s) for the accuracy parameter. Then the decision system will instruct the measurement system to acquire the measurement data until all the data is acquired with error less than the specified accuracy. In another example, if the user sets a maximum time to acquisition and the measurement has taken more than this predefined maximum time, the decision system will complete the remaining measurements without reacquiring the measurements acquired in the wrong locations. Because motion is determined for a single measurement or multiple measurements associated with a single image frame, the measurement(s) associated with a particular image frame could be re-acquired if the decision system determines that motion was unacceptable only for a specific image frame in the case of a brief saccade, and after reacquiring the corresponding measurements, the measurement system would proceed to the next un-measured location and continue data acquisition with the latest offsets from the tracking system. Alternatively, if the decision system detects unacceptable displacements for a series of image frames, multiple measurements would be retaken.

In another embodiment, the decision system might decide to keep or re-take an OCT scan based on whether the top and bottom of the tissue detected from the scan is within limits in the axial or z-direction to ensure that the tissue was completely captured in the scan. The decision system could also use the information of whether there was a reflection in the OCT data to make a decision about re-scanning.

One key aspect of the present invention is that the measurement system is not constrained by the tracking system or the decision system. Only when the decision system indicates that a particular measurement or data point is not good is the measurement system directed to go back and retake the scan with the offsets provided. Otherwise, it continues to collect data at predefined points. This is an important difference from prior art retinal tracking systems, where the measurement system either does not proceed until it has acquired data at the current location when the retina is reasonably stable or where an "active" tracker keeps the retina relatively stable as determined by the measurement system throughout the duration of the scan. This distinction allows there to be a lag time between when the eye moves and when the tracker identifies that the eye has moved while continuing to collect data which might be used, providing an efficient way to collect reduced motion measurement data.

User Interface (UI) System

The user interface system 106 could consist of a computer display with a graphical user interface, keyboard, mouse, joystick etc but is not limited to these devices. The graphical user interface (GUI or UI) displays different elements to give feedback to the user about the tracking as well as prompt the user for different actions as needed. A User Interface System for efficiently displaying OCT imaging data was described in US Publication No. 2008/0100612 hereby incorporated by reference. The current invention introduces new UI elements that allow the user to control the retinal tracking based on preset values as well as in real-time so that the data can be acquired in the most efficient fashion. One embodiment of the current system using an OCT measurement system is described below. However the concepts can be generalized to any measurement and imaging systems. The main elements of the UI as they pertain to this invention are described below. Not all elements need be included.

Figure 8:
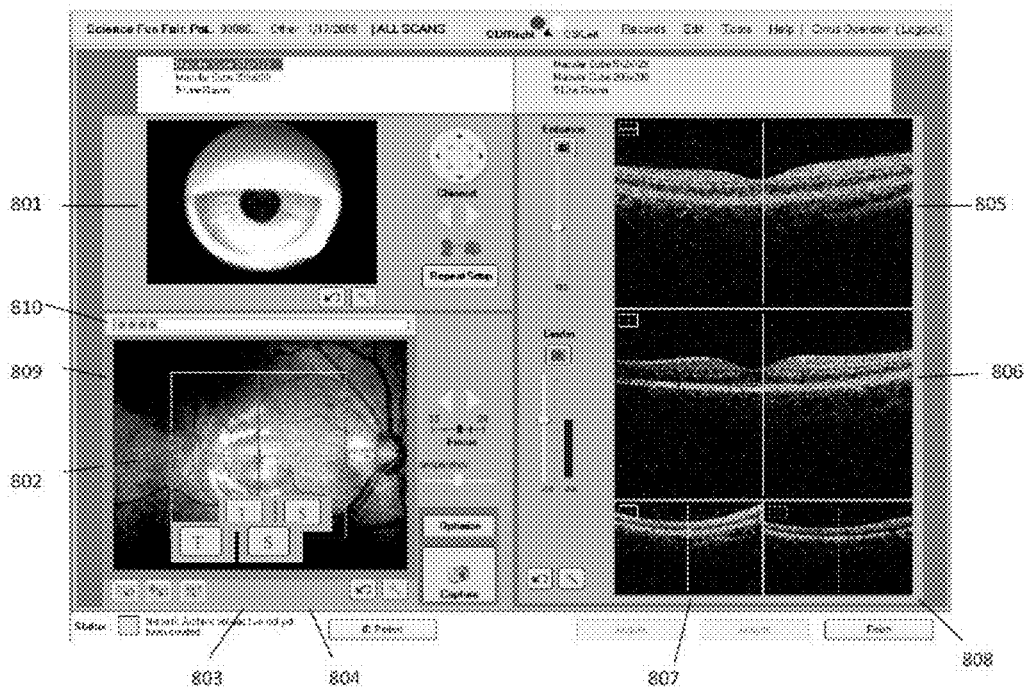
FIG. 8 is a sample user interface displaying key aspects of the invention and how they would be displayed and controlled by the instrument user.
Figure 9:
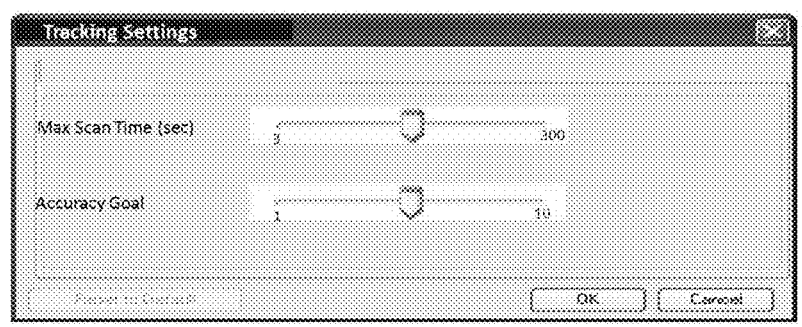
FIG. 9 is an additional component of the user interface to provide user input regarding parameters of the tracking system.

1) A live display of the images from the fundus imaging system during alignment and during acquisition.
2) Display of fundus image quality: The quality of the fundus image from the live stream could be displayed to the user. It could be a numerical display or a graphical display (bar graph, line graph etc). This display will allow the user to adjust the patient alignment to get better fundus images during alignment. This display will also especially be useful if the tracking is unable to progress because of low quality fundus images and the feedback mechanism prompts the user to better align the patient to acquire improved quality fundus images or to turn off tracking if the quality cannot be improved due to anatomical conditions of the subject being imaged. In addition to the quality of the current live fundus image, the quality of the reference image from the previous scan could also be displayed (if the tracker is being used to go back to the same location of the previous scan). This will be a static display but will give the operator feedback about the probability of the tracking being successful using a fundus image from the previous scan with a certain quality.
3) A live display of the measurement data (OCT B-Scans in this example): This will be a live display of the OCT B-Scans as they are acquired. This gives the user the ability to see what data is being acquired.
4) An indicator (button, box, border etc) that indicates if tracking is successful in the x-y direction.
5) An indicator (button, box, border etc) that indicates if tracking is successful in the z-direction
6) An indicator (number, bar, line etc) about the progress in taking measurement data. For example this could be a numerical display of the scan progress in percentage format or a status bar.
7) A set of user controls that allow the user to change the alignment of the patient during acquisition. This could include positioning the OCT beam to go through the proper pupil location, changing the focus of the fundus image, adjusting the chinrest of the instrument, positioning the OCT image in z-direction etc.
8) A display element overlaying the location of where the measurement data is being acquired on the live fundus image. For example in a cube scan, a box could move on the live fundus image to indicate where the data is currently being acquired.
9) A display of the en face image using the OCT cube data as data is being acquired and overlaying it on the fundus image. This could also serve as a visual indicator of scan progress since portions of the cube that have already been acquired will be filled in and portions to be acquired will be blank.
10) In the case of z-tracking failure due to the image hitting the bottom or top of the field of view in z, or the image not in view, an indicator prompting the user to move in the positive or negative z-direction to get the image back in range.
11) An option for the user to input expected accuracy parameters for the tracker along the x-y dimensions and the z-dimension. This could be accomplished in many ways including but not limited to through a numerical input using a keyboard, a knob, a slider bar, or one or more buttons.
12) An input option for the user to change the accuracy parameters during the scan as needed.
13) A user controlled input to stop all tracking. This could be a button or switch and could be activated in the middle of the scan if so desired. The system would still complete the scan without tracking if this was the case.
14) A user controlled input to stop the tracking in z-dimension only if so desired. The system would complete the scan with only x-y tracking in this case
15) A user controlled input to stop the tracking in x-y dimension only if so desired. The system would complete the scan with only z tracking in this case
16) A user controlled input to specify the maximum time for acquisition of a scan. If the scan takes longer than the specified maximum time, the system would automatically switch off tracking and complete the scan Components of a sample user interface incorporating some of the above options are shown in FIGS. 8 and 9. The alignment with respect to the pupil of the eye of the patient is shown in the upper left hand window of the display 801 while the live stream of fundus images is displayed in the bottom left window 802. The controls next to window 801 allow adjustments to the positioning of the instrument relative to the patient and could lead to possible improvements in fundus image quality. An adjustable colored frame 809 and a live quality indicating bar 810 are used to indicate the quality of each image from the fundus imager. The frame could be colored green when the frame is of high enough quality to be used for tracking and changed to red if the quality falls below some predetermined threshold. Button 803 allows the user to turn tracking on or off while button 804 activates a pop up window as shown in FIG. 9 that allows the user to input the maximum scan time in seconds and an overall accuracy value for the tracking on a scale of 1-10. B-scans 805 and 806 correspond to the horizontal and vertical lines making up the cross hairs shown in the center of fundus image 802 while B-scans 807 and 808 correspond to the top and bottom horizontal lines shown on the fundus image.

Results

Figure 10:
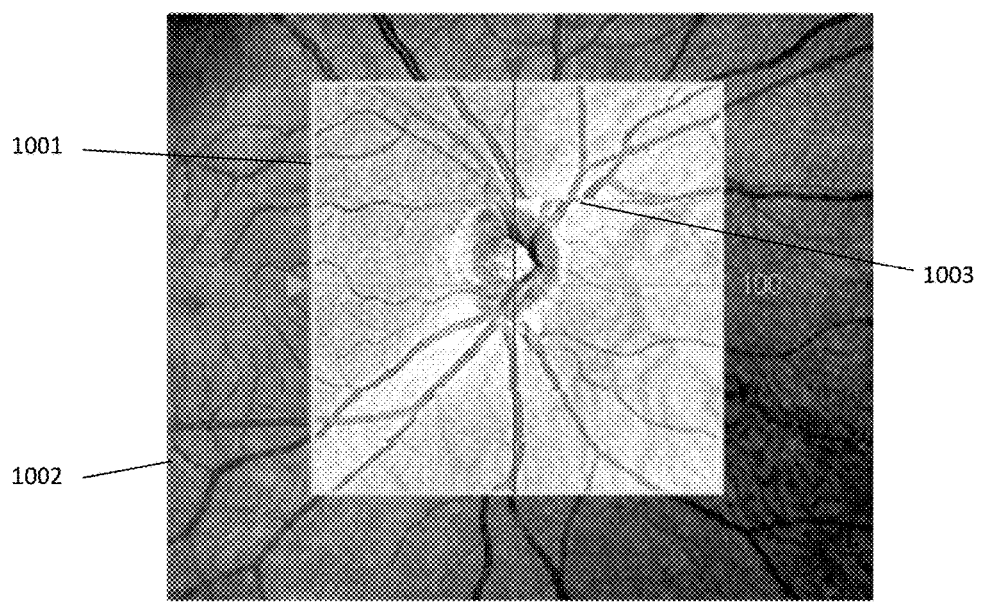
FIG. 10 shows an OCT fundus image generated from OCT measurement data overlaid with a fundus image from an imaging system where the measurement data was taken without tracking the motion of the eye.
Figure 11:
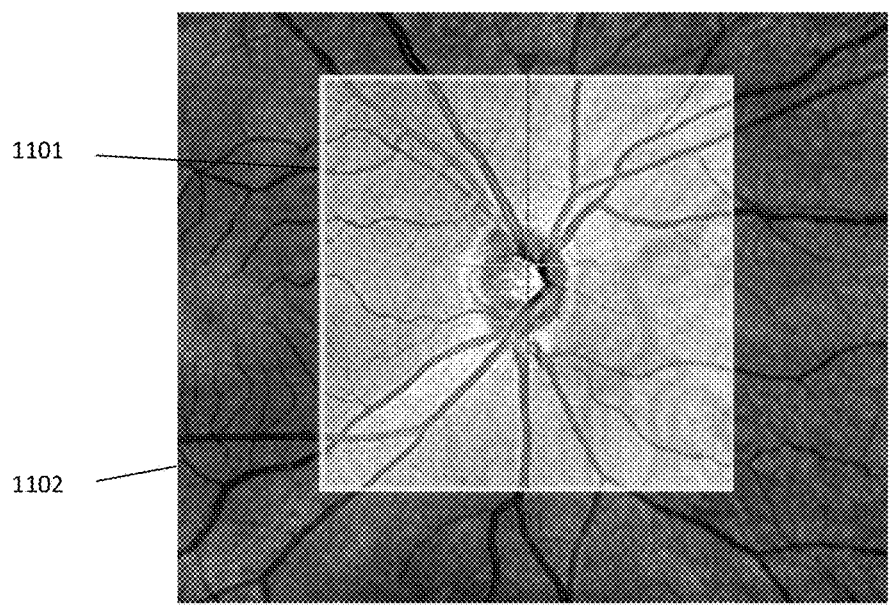
FIG. 11 shows an OCT fundus image generated from OCT measurement data overlaid with a fundus image from an imaging system where the measurement data was taken with tracking the motion of the eye.

FIGS. 10 and 11 show the comparative advantage of some aspects of the invention using the OCT and LSO system. FIG. 10 shows an OCT en face image 1001 (generated from an OCT volume by partial integration of intensity values along the z-dimension for each pixel in x-y according to techniques described in U.S. Pat. No. 7,301,644 hereby incorporated by reference) overlaid on a fundus image generated from the LSO 1002. In this figure, the OCT data was acquired without tracking. The effect of patient motion during the scan is clearly visible as breaks in the blood vessels in the OCT enface image 1003. FIG. 11 shows an OCT en face image 1101 overlaid on a fundus image 1102 acquired on the same patient with tracking in the x and y dimensions. The effect of patient motion during the scan has been reduced and the blood vessels appear continuous.

Figure 12:
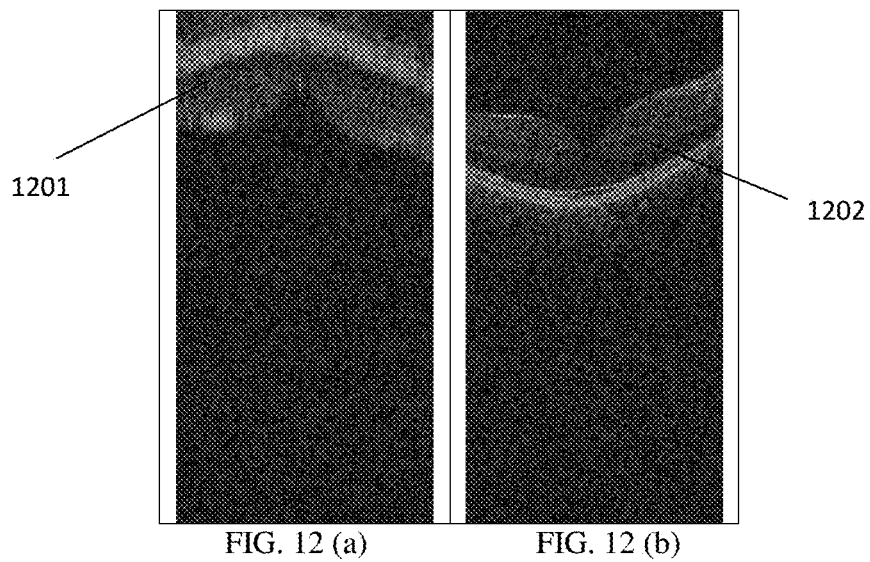
FIG. 12(a) shows mirror image OCT data than can result when there is patient motion and tracking in the axial direction is not performed.
FIG. 12(b) shows OCT data collected with axial motion tracking leading to a higher quality and physiological meaningful image.

FIG. 12 shows the improvement in an OCT image due to the z-tracking along the z or axial dimension of the scanning. The left panel denoted 12(a), shows a B-Scan acquired with a non-tracking OCT system. Since the patient moved in z, a mirror, or inverted image 1201 was acquired by the system. The right panel denoted 12(b) shows a B-Scan 1202 of the same eye acquired with a system that had z-tracking as described in this invention. Even though similar patient motion was present in both the scans, the system with z-tracking is able to detect mirror images and accept only the good images, resulting in superior image quality representing the actual physiology of the eye.

Although various embodiments that incorporate the teachings of the present invention have been shown and described in detail herein, those skilled in the art can readily devise many other varied embodiments that still incorporate these teachings.

The following references are hereby incorporated by reference:

US PATENT DOCUMENTS

U.S. Pat. No. 4,856,891 Pflibsen et al. "Eye fundus tracker/stabilizer"
U.S. Pat. No. 5,321,501 Swanson et al. "Method and apparatus for optical imaging with means for controlling the longitudinal range of the sample"
U.S. Pat. No. 5,920,373 Bille "Method and apparatus for determining optical characteristics of a cornea"
U.S. Pat. No. 5,975,697 Podoleanu et al. "Optical mapping apparatus with adjustable depth resolution"
U.S. Pat. No. 6,325,512 Wei "Retinal tracking assisted optical coherence tomography"
U.S. Pat. No. 6,655,805 Fujieda et al. "Ophthalmic apparatus"
U.S. Pat. No. 6,726,325 Xie et al. "Tracking assisted optical coherence tomography"
U.S. Pat. No. 6,736,508 Xie et al. "Tracking assisted optical procedure"
U.S. Pat. No. 7,113,818 Rogers et al. "Apparatus for high resolution imaging of moving organs"
U.S. Pat. No. 7,301,644 Knighton et al. "Enhanced optical coherence tomography for anatomical mapping"
U.S. Pat. No. 7,330,270 O'Hara et al. "Method to suppress artifacts in frequency-domain optical coherence tomography"
U.S. Pat. No. 7,365,856 Everett et al. "Method of motion correction in optical coherence tomography imaging"
U.S. Pat. No. 7,404,640 Ferguson et al. "Monitoring blood flow in the retina using a line-scanning laser ophthalmoscope"
U.S. Pat. No. 7,458,684 Fukuma et al. "Fundus observation device"
U.S. Pat. No. 7,527,378 Fukuma et al. "Fundus observation device"
U.S. Pat. No. 7,480,396 Teiwes et al. "Multidimensional eye tracking and position measurement system for diagnosis and treatment of the eye"
U.S. Pat. No. 7,643,154 Tsutomu et al. "Optical image measurement device"
U.S. Pat. No. 7,756,311 Yasuno et al. "Optical image measuring device, optical image measuring program, fundus observation device, and fundus observation program"
U.S. Pat. No. 7,777,893 Tsutomu et al. "Optical image measurement device"
U.S. Pat. No. 7,789,511 Hiroyuki et al. "Eye movement measuring apparatus, eye movement measuring method and recording medium."
U.S. Pat. No. 7,805,009 Everett et al. "Method and apparatus for measuring motion of a subject using a series of partial images from an imaging System"
US Patent Publication No. 2005/0270486 Teiwes et al. "Method and apparatus for image-based eye tracking for retinal diagnostic or surgery device"
US Patent Publication No. 2009/0141240 Weitz et al. "Method for performing micro-perimetry and visual acuity testing"
US Patent Publication No. 2010/0053553 Zinser et al. "Method and apparatus for retinal diagnosis"
US Patent Publication No. 2007/0291277 Everett et al. "Spectral domain optical coherence tomography system"
US Patent Publication No. 2010/0118132 Tsutomu et al. "Optical measurement device"

OTHER PUBLICATIONS

Podoleanu et al. "Combined multiplanar optical coherence tomography and confocal scanning ophthalmoscopy" Journal of Biomedical Optics 9(1): 86-93 2004.
Ip et al. "Fundus based eye tracker for optical coherence tomography" Proceedings of IEEE EMBS 2:1505-8 2004.

What is claimed is:

1. A method for acquiring optical coherence tomography (OCT) data of an eye of a subject in the presence of motion, said method comprising:
   a) collecting a plurality of OCT B-scans at locations across the eye of the subject using an OCT system;
   b) concurrently collecting images of the retina of the subject using a fundus imaging system different from the OCT system such that each OCT B-scan has a corresponding image frame;
   c) comparing each image frame to a reference image frame to determine the amount of eye movement that occurred during the collection of a particular B-scan;
   d) collecting a replacement B-scan when the determined amount of eye movement associated with the acquisition of the particular B-scan exceeds a predetermined threshold, wherein during step (c), continuing to perform step (a) until a determination is made to collect a replacement B-scan;
   e) generating an image from the OCT data; and
   f) storing or displaying the image.

2. A method as recited in claim 1, where the OCT data is collected across the retina of the eye of the subject.

3. A method as recited in claim 1, further comprising assessing the quality of each image frame prior to the comparing step wherein the quality of the image frame is based on at least one of the brightness, uniformity of illumination, level of focus, and contrast of the image frame.

4. A method as recited in claim 3, further comprising using an image frame as the reference frame for future comparisons if the quality of the image frame exceeds the quality of the reference frame.

5. A method as recited in claim 3, wherein the quality of the image frame is assessed by analyzing one or both of: the intensity of the image or the focus of the image.

6. A method as recited in claim 3, further comprising disabling the comparing and collecting steps if the quality of the image frames fall below a predetermined image quality threshold.

7. A method as recited in claim 1, further comprising assessing the quality of the image frames to determine the reference frame and enable the comparing and collecting replacement data steps.

8. A method as recited in claim 1, further comprising using an image frame as the reference frame for subsequent B-scans if a significant eye movement is detected.

9. A method as recited in claim 2, wherein the images of the retina are collected using a line-scan imager.

10. A method as recited in claim 2, wherein the images of the retina are collected using a confocal scanning laser ophthalmoscope.

11. A method as recited in claim 1, wherein the predetermined threshold is defined by the user.

12. A method as recited in claim 1, wherein the predetermined threshold is different at different locations on the eye.

13. A method as recited in claim 1, wherein the predetermined threshold is varied depending on the OCT B-scan acquisition time.

14. A method as recited in claim 1, further comprising completing the remainder of the B-scans without collecting new replacement data if the total acquisition time exceeds a predetermined amount of time.

15. A method as recited in claim 1, further comprising comparing image frames from subsequent B-scans in addition to the image frame for a particular B-scan in determining whether to collect a replacement B-scan at a particular set of locations.

16. A method as recited in claim 1, wherein the comparing is done based on features apparent in the image frame and the reference image frame.

17. A method as recited in claim 16, wherein the best features selected for the comparison are adaptively learned.

18. A method as recited in claim 3, further comprising displaying an indication of the quality of the image frames to the user.

19. A method as recited in claim 1, wherein the reference image was collected on the subject from a prior examination or visit.

20. A method as recited in claim 1, further comprising: comparing a reference frame collected at a previous visit to a reference frame collected at the current visit; using the correspondence between the reference frame from the current visit and the image frames to determine the locations to be scanned such that the resulting OCT B-scans are collected at the same locations as a set of OCT B-scans collected at a previous visit.

21. A method as recited in claim 1, wherein the comparison is carried out on portions of the image and reference frames.

22. A method as recited in claim 1, in which the corresponding image frame for two or more B-scans is the same and replacement B-scans are collected for the two or more B-scans when the determined amount of eye movement associated with the acquisition of the two or more B-scans exceeds a predetermined eye movement threshold.

23. A system for acquiring optical coherence tomography (OCT) data in the presence of motion comprising:
   an OCT system for collecting B-scans at a plurality of locations across the retina of a subject;
   an imaging system for concurrently collecting images of the retina of the subject, such that each B-scan has a corresponding image frame; and
   a processor for comparing each image frame to a reference image frame to determine eye movement and for controlling the measurement system to collect a replacement B-scan at a particular set of locations if the eye movement during the collection of a B-scan determined by said comparison exceeds a predetermined threshold and wherein the OCT system continues to collect B-scans while the processor operates in parallel to determine if the eye movement exceeded the threshold and the collection of replacement B-scans are required.

24. A system as recited in claim 23, wherein prior to comparing the image frame to a reference frame, the processor assesses the quality of the image frame wherein the quality of the image frame is based on at least one of the brightness, uniformity of illumination, level of focus, and contrast of the image frame.

25. A system as recited in claim 24, further comprising a display for displaying an indication of the image quality of the user.

26. A system as recited in claim 23, wherein the predetermined threshold is established by the user.

27. A system as reciting in claim 23, in which the corresponding image frame for two or more B-scans is the same and replacement B-scans are collected for the two or more B-scans when the determined amount of eye movement associated with the acquisition of the two or more B-scans exceeds a predetermined eye movement threshold.

* * * * *

UNITED STATES PATENT AND TRADEMARK OFFICE
CERTIFICATE OF CORRECTION

PATENT NO. : 10,092,178 B2
APPLICATION NO. : 14/688743
DATED : October 9, 2018
INVENTOR(S) : Harihar Narasimha-Iyer et al.

Page 1 of 1

It is certified that error appears in the above-identified patent and that said Letters Patent is hereby corrected as shown below:

In the Specification

In Column 12, Line 35, delete "though out" and insert -- throughout --, therefor.

In Column 13, Line 11, delete "un-measured" and insert -- unmeasured --, therefor.

In Column 14, Line 21, delete "direction" and insert -- direction. --, therefor.

In Column 14, Line 62, delete "case" and insert -- case. --, therefor.

In Column 14, Line 65, delete "case" and insert -- case. --, therefor.

In Column 15, Line 2, delete "scan" and insert -- scan. --, therefor.

Signed and Sealed this
Eighteenth Day of December, 2018

Andrei Iancu
*Director of the United States Patent and Trademark Office*